(12) United States Patent
Han et al.

(10) Patent No.: US 8,828,238 B2
(45) Date of Patent: Sep. 9, 2014

(54) THERMOPHILIC BACTERIUM AND USES OF EXTRACELLULAR PROTEINS THEREFROM

(71) Applicant: Industrial Technology Research Institute, Hsinchu (TW)

(72) Inventors: Yin-Lung Han, Tainan (TW); Tai-Rong Guo, Zhubei (TW); Jo-Shu Chang, Taichung (TW); I-Ju Chou, Tainan (TW)

(73) Assignee: Industrial Technology Research Instiute, Hsinchu (TW)

( * ) Notice: Subject to any disclaimer, the term of this patent is extended or adjusted under 35 U.S.C. 154(b) by 0 days.

(21) Appl. No.: 13/846,224

(22) Filed: Mar. 18, 2013

(65) Prior Publication Data

US 2013/0323818 A1 Dec. 5, 2013

Related U.S. Application Data

(60) Provisional application No. 61/652,522, filed on May 29, 2012.

(30) Foreign Application Priority Data

Nov. 22, 2012 (TW) .............................. 101143616 A

(51) Int. Cl.
| | | |
|---|---|---|
| *C02F 5/08* | (2006.01) |
| *C02F 1/00* | (2006.01) |
| *C12N 1/02* | (2006.01) |
| *C12N 1/20* | (2006.01) |
| *C23F 11/14* | (2006.01) |
| *C09K 8/528* | (2006.01) |
| *C07K 14/195* | (2006.01) |
| *C12R 1/01* | (2006.01) |

(52) U.S. Cl.
CPC . *C12R 1/01* (2013.01); *C09K 8/528* (2013.01); *C12N 1/20* (2013.01); *C23F 11/14* (2013.01); *C02F 5/08* (2013.01); *C07K 14/195* (2013.01); *C12N 1/02* (2013.01)
USPC ........ 210/681; 210/696; 435/261; 435/252.1; 530/400; 530/350; 507/244

(58) Field of Classification Search
CPC ............ A61K 35/74; C12R 1/01; C02F 5/08; C12P 7/065; D06M 16/003
See application file for complete search history.

(56) References Cited

U.S. PATENT DOCUMENTS

| 4,480,036 A | 10/1984 | Morgan et al. |
| 7,093,663 B1 | 8/2006 | Bader |
| 8,192,854 B2 | 6/2012 | Borole |
| 8,202,716 B2 | 6/2012 | Thompson et al. |

OTHER PUBLICATIONS

Albuquerque et al., Systematic and Applied Microbiology, 29:450-456, 2006.*
Chen et al., Extremophiles, 10:35-40, 2006.*
Khoo et al., "Interactions of calcium and other metal ions with caldolysin, the thermostable proteinase from *Thermus aquaticus* strain T351", Biochem. J. (1984) vol. 221, pp. 407-413.

* cited by examiner

*Primary Examiner* — Jennifer McDonald
*Assistant Examiner* — Qing Xu
(74) *Attorney, Agent, or Firm* — Birch, Stewart, Kolasch & Birch, LLP

(57) ABSTRACT

A novel thermophilic bacterium is provided, which has a 16S rDNA sequence as set forth in SEQ ID NO. 1. The thermophilic bacterium excretes extracellular proteins having excellent metal-ion binding ability, being useful in the treatment of boiler equipment, pipelines, geothermal wells or industrial wastewater or hard water.

20 Claims, 13 Drawing Sheets

THERMOPHILIC BACTERIUM AND USES OF EXTRACELLULAR PROTEINS THEREFROM

CROSS REFERENCE TO RELATED APPLICATIONS

This application claims the priority of Taiwan Patent Application No. 101143616, filed Nov. 22, 2012, which claims the priority of U.S. Provisional Application No. 61/652,522, filed May 29, 2012, the disclosure of which is hereby incorporated by reference herein in its entirety.

INCORPORATION BY REFERENCE OF SEQUENCE LISTING

A sequence listing submitted as a text file via EFS-Web is incorporated herein by reference. The text file containing the sequence listing is named "0956-A24070-US_Seq_Listing.txt"; its date of creation is Mar. 1, 2013; and its size is 2,129 bytes.

TECHNICAL FIELD

The technical field relates to a novel thermophilic bacterium and uses of extracellular proteins therefrom.

BACKGROUND

Geothermal energy is an abundant green energy from the Earth and has potential for development. However, due to its unique components, a change of temperature or pressure may easily cause geothermal fluids to form scales on the wellbore walls or in the formation fractures, which increases the instability of geothermal fluid production.

An acid or chemical treatment has been internationally used against geothermal scale formation. However, the waste fluids left from the acid or chemical treatment cause severe environmental pollution. Therefore, development of green energy with high production efficiency, while being environmentally friendly, is being researched more and more.

SUMMARY

A detailed description is given in the following embodiments with reference to the accompanying drawings.

In one embodiment, the disclosure provides an isolated thermophilic bacterium, *Tepidimonas fonticaldi* sp. nov., internationally deposited in the Korean Collection of Type Culture (KCTC) with the deposit number of KCTC 23862.

In another embodiment, the disclosure provides a method for inhibiting salt formation, which comprises contacting an extracellular protein(s) from an isolated thermophilic bacterium with a metal ion-containing solution to form a complex of the protein and the metal ion. The isolated thermophilic bacterium is *Tepidimonas fonticaldi* sp. nov., internationally deposited in the Korean Collection of Type Culture (KCTC) with the deposit number of KCTC 23862.

In another embodiment, the disclosure provides a method for treating high temperature wastewater, which comprises contacting an extracellular protein(s) from an isolated thermophilic bacterium with a metal ion-containing solution to form a complex of the protein and the metal ion. The isolated thermophilic bacterium is *Tepidimonas fonticaldi* sp. nov., internationally deposited in the Korean Collection of Type Culture (KCTC) with the deposit number of KCTC 23862.

BRIEF DESCRIPTION OF THE DRAWINGS

The present invention can be more fully understood by reading the subsequent detailed description and examples with references made to the accompanying drawings, wherein:

Figure 6:
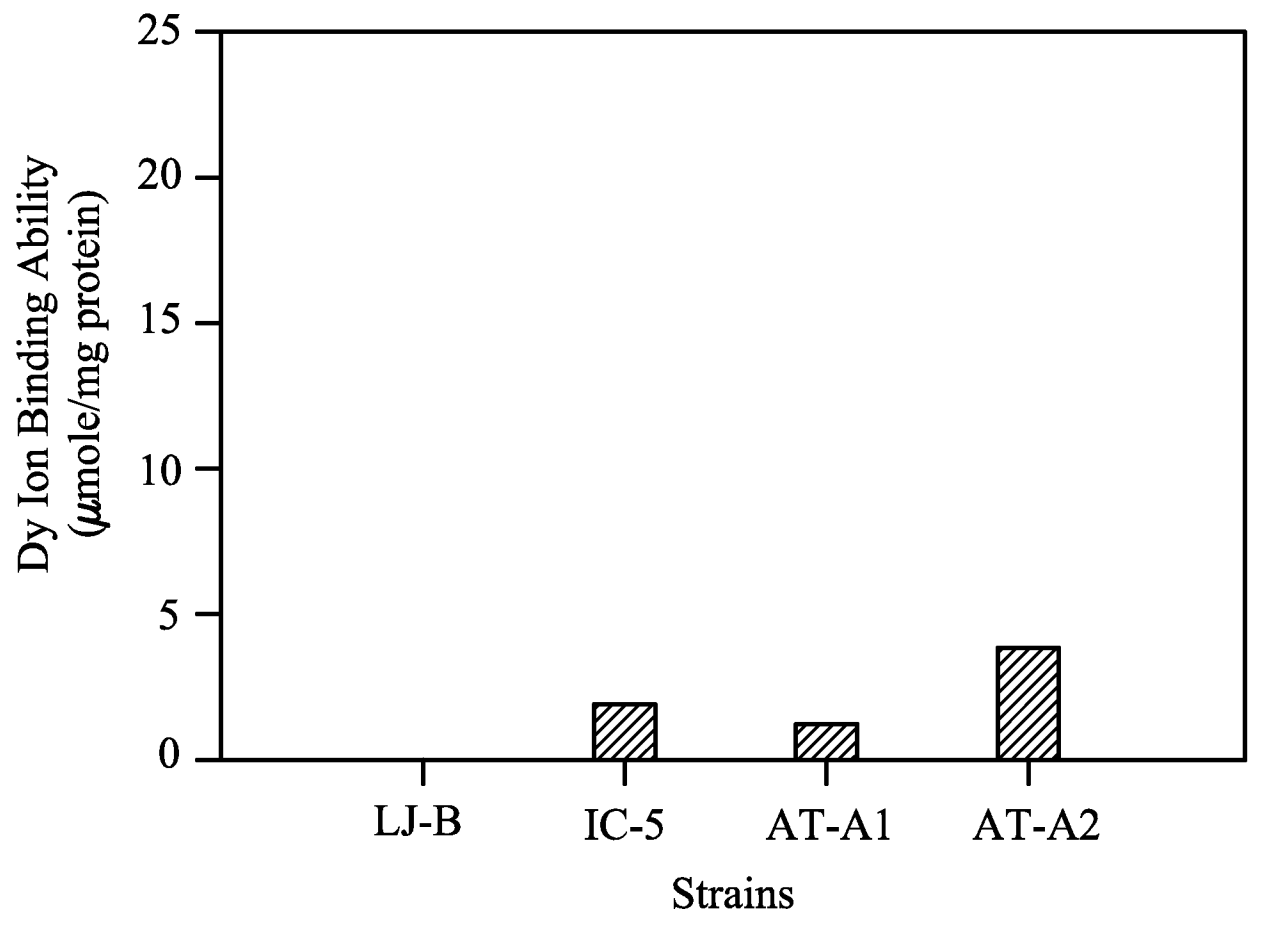

FIG. 6 is a bar graph showing the dysprosium (Dy) ion binding ability of extracellular proteins of several thermophilic strains;

Figure 7:
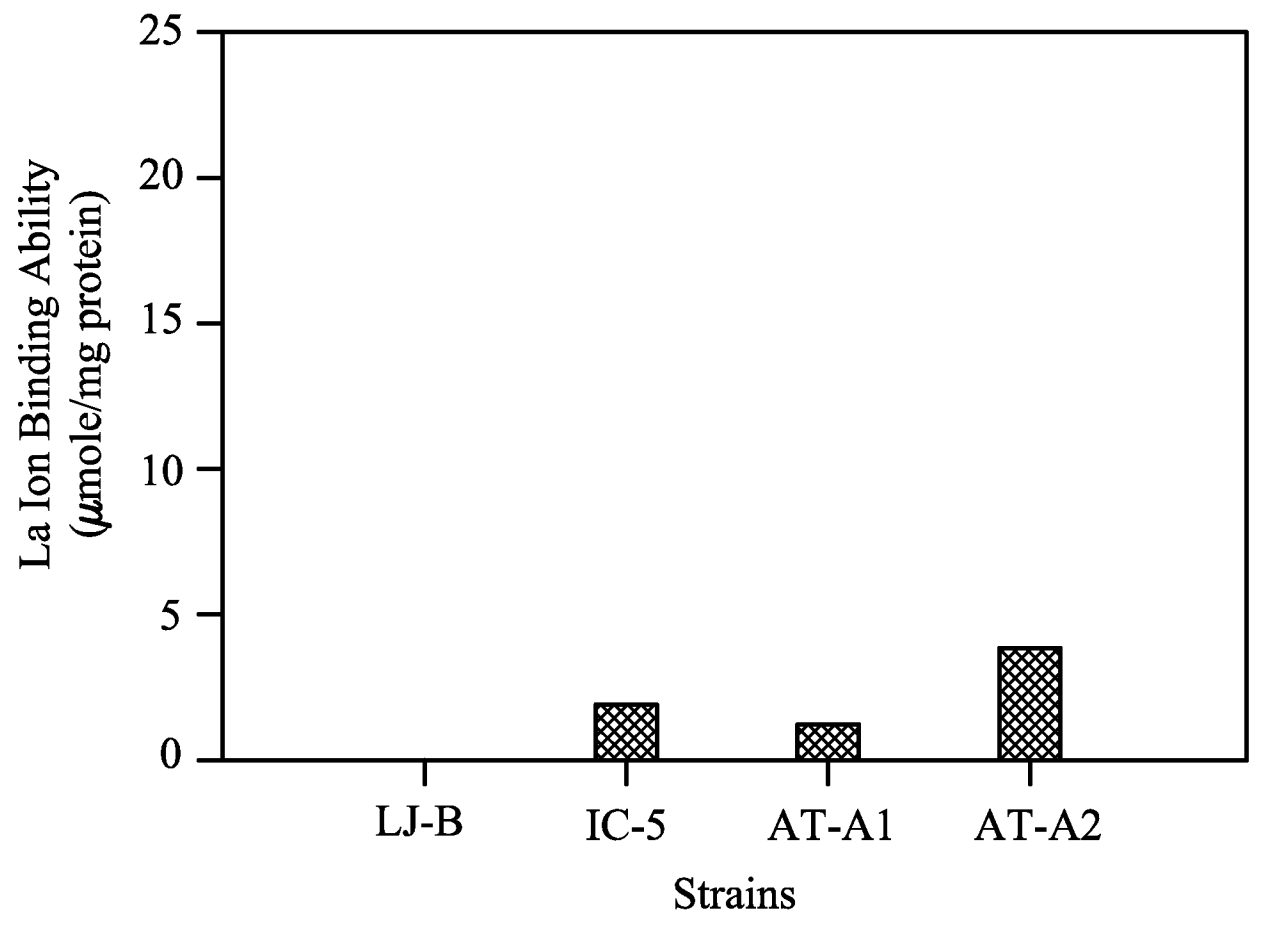

FIG. 7 is a bar graph showing the lanthanum (La) ion binding ability of extracellular proteins of several thermophilic strains;

Figure 10:
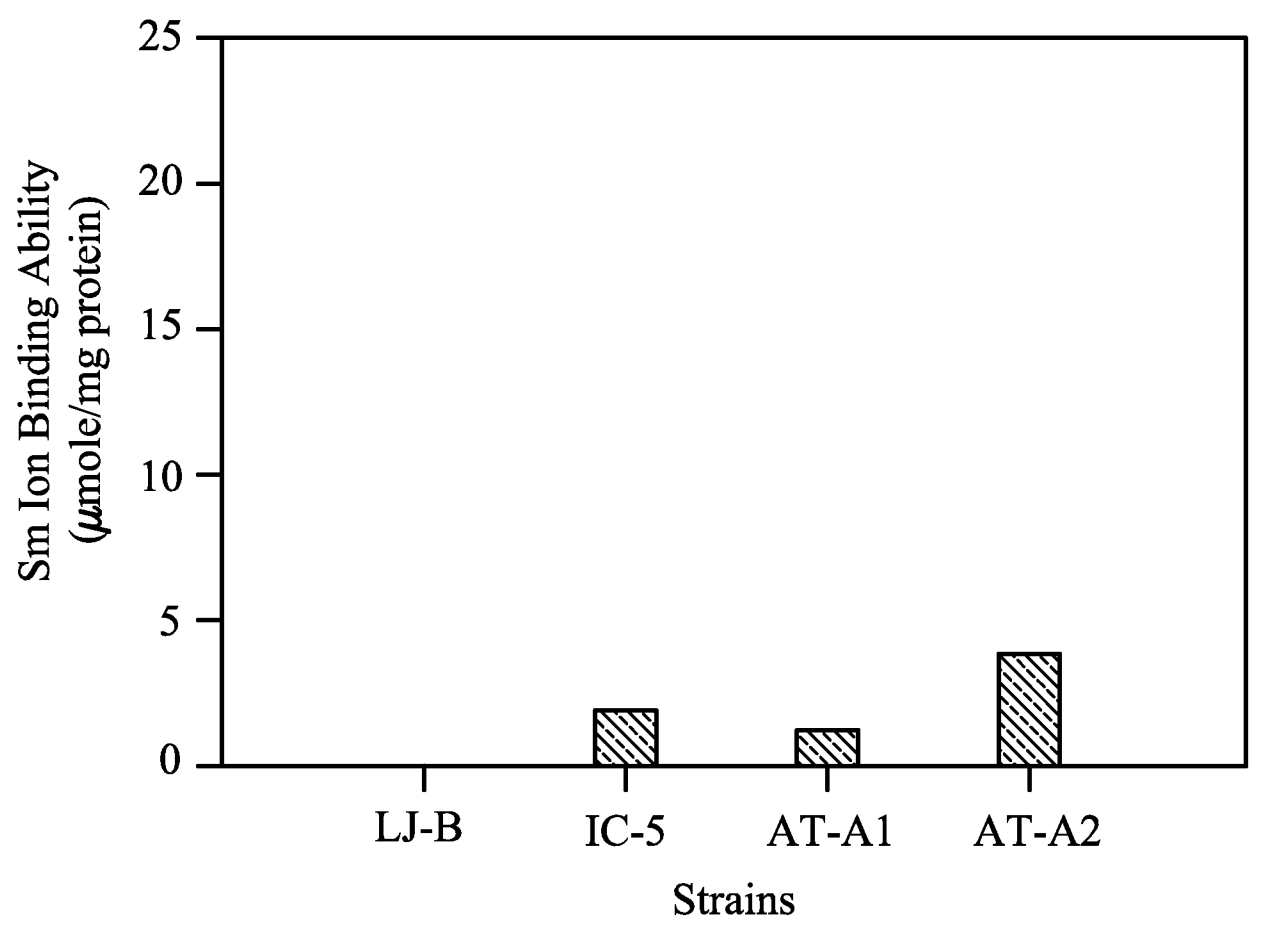

FIG. 10 is a bar graph showing the samarium (Sm) ion binding ability of extracellular proteins of several thermophilic strains;

Figure 11:
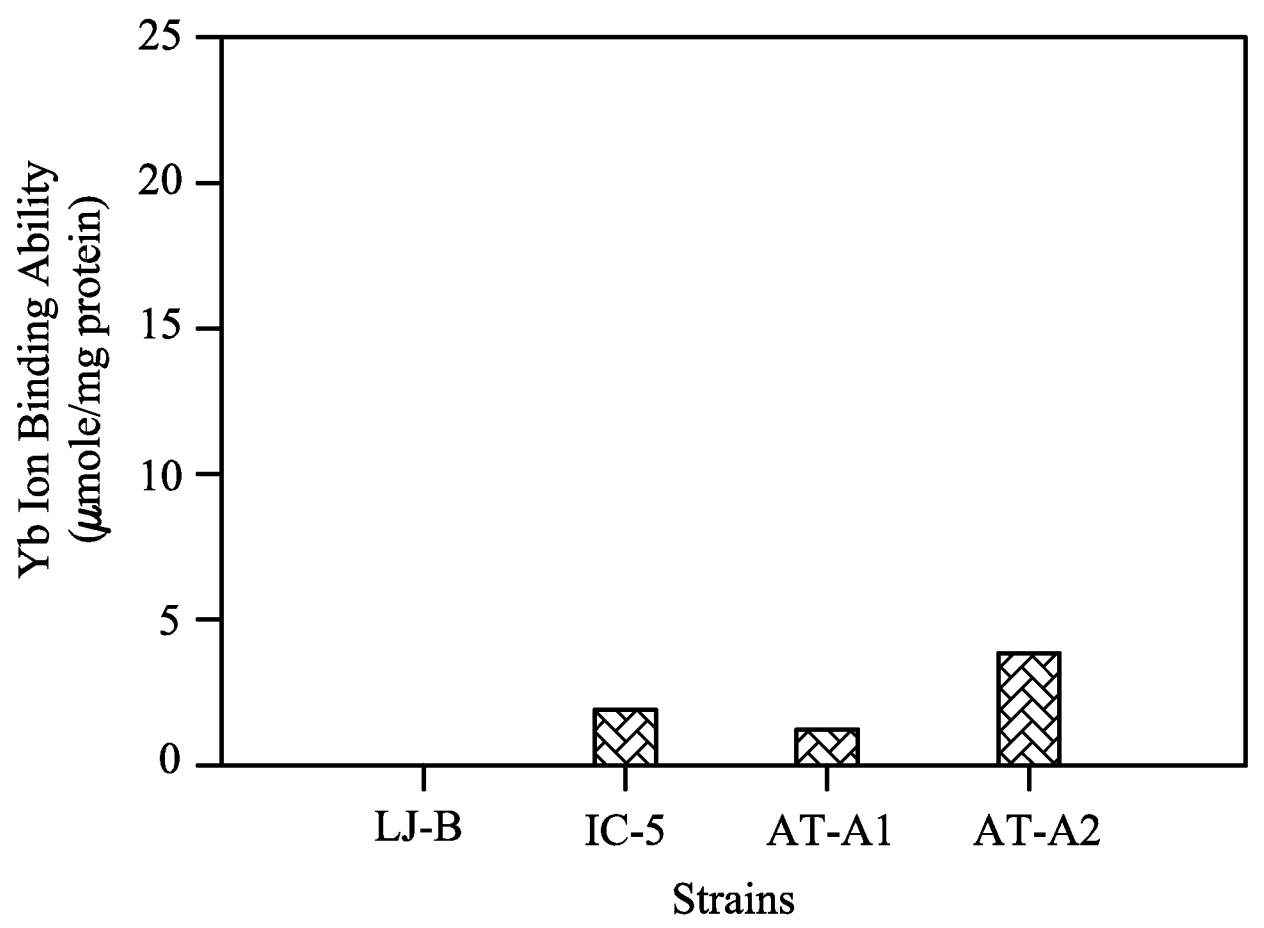

FIG. 11 is a bar graph showing the ytterbium (Yb) ion binding ability of extracellular proteins of several thermophilic strains;

DETAILED DESCRIPTION

Figure 1:
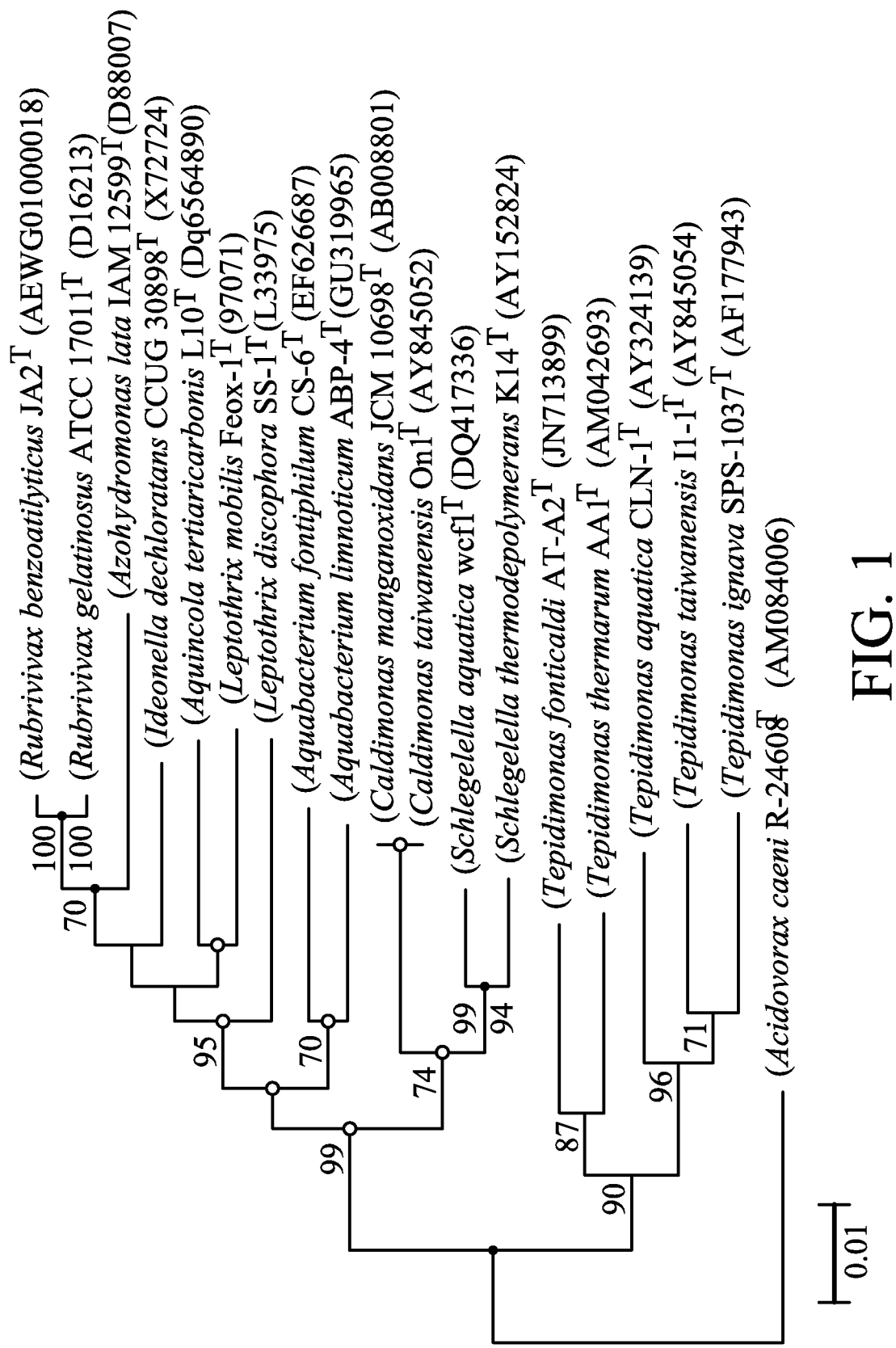
FIG. 1 shows a phylogenic tree diagram of *Tepidimonas fonticaldi* sp. nov., based on the similarity of 16S rDNA; in which "*Tepidimonas fonticaldi* AT-A2T (JN713899)" represents the strain, *Tepidimonas fonticaldi* sp. nov., disclosed in the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment, the present disclosure provides a novel thermophilic bacterium isolated and purified from hot spring water at the Antun, Hualien County, Taiwan. The isolated thermophilic bacterium, after being analyzed and sequenced, shows a sequence of the 16S ribosomal DNA (rDNA) as set forth in SEQ ID No. 1. According to the sequence of the 16S rDNA, the isolated strain shows phylogenetically close to the well-known strains, *Tepidimonas thermarum* AA-1$^T$ (97.5% sequence similarity), *Tepidimonas aquatica* CLN-1$^T$ (96.8% sequence similarity), *Tepidimonas ignava* SPS-1037$^T$ (96.4% similarity) and *Tepidimonas taiwanensis* I1-1$^T$ (95.8% sequence similarity). A phylogenetic tree diagram based on the sequence similarity of 16S rDNA is depicted in FIG. 1.

The 16S rDNA sequences of the isolated thermophilic strain and *Tepidimonas thermarum* AA-1$^T$ were made to hybridize. A DNA-DNA relatedness was shown as 23.9±0.2%, indicating that the isolated thermophilic strain belonged to *Tepidimonas* sp.

On the biological characteristics, the isolated thermophilic bacterium shows aerobic and Gram negative, and forms non-pigmented colonies and mobiles by a single polar flagellum. An optimal growth occurs at 35~60° C., or 55° C., at 0~1.0 wt % of NaCl, or 0.2 wt % of NaCl, and under a pH 7.0~9.0, or pH 7.0. The predominant cellular fatty acids of the isolated thermophilic strain include $C_{16:0}$ (40.2%), summed feature 3 ($C_{16:1}$ ω7c and/or $C_{16:1}$ ω6c; 20.1%) and $C_{17:0}$ cyclo (11.5%). The major polar fatty acids include phosphatidylethanolamine (PE) and phosphatidylglycerole (PG). The GC content of the total DNA in one cell of the bacterium is 70.1 mol %.

On the basis of the phylogenetic and phenotypic data, the isolated strain is classified as a novel species and named as *Tepidimonas fonticaldi* sp. nov., internationally deposited in the Korean Collection of Type Culture (KCTC) on Jan. 10, 2012 with the deposit number of KCTC 23862. It was also deposited in the Bioresource Collection and Research Center (BCRC) of Taiwan on Nov. 21, 2011 with the deposit number of BCRC 80391 and was also deposited in the Laboratorium voor Microbiologie Gent' Belgium (LMG) on Nov. 28, 2011 with the deposit number of LMG 26746.

The isolated thermophilic bacterium, *Tepidimonas fonticaldi* sp. nov., extracellularly excretes proteins under an appropriate condition. The extracellular proteins have excellent metal ion binding ability and are not affected by high temperatures, high pressure and/or extreme pH conditions. Specifically, in one example, the extracellular proteins show excellent metal ion binding ability under a temperature of 75~150° C., or 125~150° C., at 1 atmosphere (atm), pH 7. In another example, the extracellular proteins show excellent metal ion binding ability under a pressure of 1~50 atm, or 10~30 atm, at 25° C., pH 7. In another example, the extracellular proteins show excellent metal ion binding ability at pH 2~10, or pH 7~10, at 25° C., 1 atm.

The metal ion binding ability is preferably bindings to bi- or tri-valent metal ions. The bi- or tri-valent metal ions may comprise cerium (Ce), dysprosium (Dy), erbium (Er), europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb), yttrium (Y), silver (Ag), aluminium (Al), boron (B), barium (Ba), bismuth (Bi), calcium (Ca), cadmium (Cd), cobalt (Co), chromium (Cr), copper (Cu), iron (Fe), gallium (Ga), indium (In), potassium (K), lithium (Li), magnesium (Mg), manganese (Mn), sodium (Na), nickel (Ni), lead (Pb), strontium (Sr), thallium (Tl), zinc (Zn) or combinations thereof, but are not limited thereto.

Due to the excellent metal ion binding ability, the extracellular proteins are able to compete with acid ions in the solution for binding with metal ions. Therefore, the metal salt formed by acid ions binding with metal ions can be reduced so that the scales formed from the metal salts can be inhibited.

Accordingly, one embodiment of the present disclosure provides a method for inhibiting salt formation, comprising contacting the extracellular protein(s) with a metal ion-containing solution to form a complex of the protein(s) and the metal ion(s).

Another embodiment of the present disclosure provides a method for treating high temperature wastewater by contacting the extracellular protein(s) with metal ion-containing wastewater to form a complex of the protein(s) and the metal ion(s).

Generally, in high temperature conditions, such as geothermal waters, boiler solutions or industrial waste or hard water, acid ions in the water or solutions ordinarily bind to metal ions to form metal salts, like calcium carbonate ($CaCO_3$), which produces scales on the walls of machines, mechanical tubes, water pipelines or the like, which leads to obstruction or damage. This causes operation of the machinery to be difficult or even damaged during high temperatures.

On the contrary, according to the present invention, the extracellular proteins is able to prevent scale formation, especially $CaCO_3$, on the walls of boiler instruments, mechanical tubes, water pipelines, geothermal wells, industrial wastes or hard waters or the like due to its excellent metal ion binding ability. Therefore, machinery can be well operated in high temperatures, under high pressure or during extreme pH conditions. The operation period and cost can be reduced accordingly. In addition, instead of acid or chemical reagents, the extracellular proteins of the present disclosure can prevent environmental pollution from the acidic or chemical treatment. Thus, the extracellular proteins of the present disclosure are useful in the treatment of boiler equipment, mechanical tubes, water pipelines, geothermal wells, industrial wastewater or hard water or the like.

Example 1

Collection and Identification of *Tepidimonas fonticaldi* sp. nov.

Collection

10 L of the hot spring water at the Antun, Hualien County, Taiwan was collected with an aluminum foil-wrapped bottle. The collected hot spring water was filtered through a 0.45 μm filter membrane under a sterile condition. The filter membrane was then put onto a 1.5% agarose medium (a mixture of 300 mL of hot spring water and 4.5 g of agarose, under 121° C., heated for 15 minutes and added into a medium plate for cooling) and cultured at 55° C. for 7~14 days. After being cultured, colonies with various colors or shapes were picked up with a sterile inoculating loop and lined on a fresh agarose medium. The steps above were repeated to obtain a pure strain. The isolated strain was stored at 4° C.

Bacteria DNA Extraction

The isolated strain was picked up from the medium with a sterile inoculating loop and added into 1 mL of sterile water. After three times of being washed with sterile water, the genomic DNA of the isolated strain was extracted by using a genomic DNA extraction minoprep system (Blood & Tissue). The extracted genomic DNA was then stored at −20° C.

16S rDNA Sequencing

The extracted genomic DNA underwent a polymerase chain reaction (PCR) following the conditions set forth in Tables 1 and 2 with a universal prokaryotic 16S ribosome PCR primer pair of FD1 (5'-AGA GTT TGA TCC TGG CTC AG-3', SEQ ID NO:2) and RD1 (5'-AAG GAG GTG ATC CAG CC-3', SEQ ID NO:3) for amplifying the 16S rDNA sequence of the isolated strain. The amplified 16S rDNA was sequenced by Mission Biotech Incorporation, Taiwan.

TABLE 1

PCR Reagents

| Reagents | Volume (μl) |
|---|---|
| DNA templates | 1 |
| Taq buffer (10 X) | 2.5 |
| Taq polymerase (2.5 U/μl) | 0.125 |
| dNTP (2.5 mM) | 2 |
| Forward primer (100 pmol/μl) | 1 |
| Reverse primer (100 pmol/μl) | 1 |
| deionized water | 17.5 |
| Total volume | 25 |

TABLE 2

PCR Conditions

| | Temperature and time | Reaction | Cycle numbers |
|---|---|---|---|
| Stage 1 | 95° C. 5 min | Denature | 1 |
| Stage 2 | 95° C. 1 min | Denature | 35 |
| | 56° C. 1 min | Annealing | |
| | 72° C. 1 min | Extending | |
| Stage 3 | 72° C. 4 min | Extending | 1 |

Alignment of 16S rDNA Sequence

The 16S rDNA sequence of the isolated strain was aligned with the GenBank library by using BLAST software (www.ncbi.nlm.nih.gov) and similarities with the published sequences in the library were analyzed. The 16S DNA sequence of the isolated strain was recorded in the NCBI (www.ncbi.nlm.nih.gov) with a series number of JN 713899, named *Tepidimonas fonticaldi* sp. nov.

Construction of the Phylogenic Tree

According to the sequence similarity obtained above, a phylogenic tree diagram was depicted with accession numbers of each strain by using BioEdit software and CLUSTAL_X and homology among these strains was calculated as well. The phylogenic tree diagram is shown in FIG. 1, in which the isolated strain was identified as *Tepidimonas fonticaldi* sp. nov.

Example 2

Metal Ion Binding Ability of Extracellular Proteins

Protein Collection

The isolated strain, *Tepidimonas fonticaldi* sp. nov., and a modal strain, *Thermus aquaticus* BCRC 17110, were respectively inoculated in a 100 mL 1/10 TSB medium (1.7 g/L pancreatic digest of casein, 0.3 g/L enzymatic digest of soybean meal, 0.25 g/L dextrose, 0.5 g/L NaCl and 0.25 g/L dipotassium phosphate) and cultured at 200 rpm, at 55° C. for 3~5 days.

The cultured medium was centrifuged at 10,000 rpm for 10 minutes. The supernatant was collected and concentrated by 10 times with a protein concentration system. The concentrated protein was taken as the extracellular proteins for the next steps. Meanwhile, the precipitate of the centrifuged medium was ultrasound vibrated to break the bacteria and the solution was taken as the intracellular proteins for the next steps.

Protein Quantification

The extracellular proteins solution obtained above 100 μL were added with a Bio-Rad protein test reagent 400 μL for a color reaction, occurring within 15 minutes. The absorbance at a wavelength of 595 nm was detected and the protein concentration was calculated.

$Ca^{2+}$ Binding Ability of Extra- and Intra-Cellular Proteins

The experiment was designed for investigating the $Ca^{2+}$ binding ability of the extra- and intra-cellular proteins. The extra- and intra-cellular proteins from the thermophilic bacteria listed in Table 3 were all detected for the $Ca^{2+}$ binding ability.

50 ppm of the extra- and intra-cellular proteins obtained from the thermophilic bacteria listed in Table 3 were respectively mixed with the 100 ppm calcium ion solution prepared by $CaCl_2 \cdot 2H_2O$ in a ratio of 1:1. The mixture was heated in 100° C. of a water bath for 1 hour. The mixture was then filtered through an ultrafiltration system with a 3 KDa membrane to capture the proteins. The filtrate was then diluted with deionized water to reach the detection limit (0~5 ppm). The $Ca^{2+}$ concentration left in the filtrate was analyzed by an inductively coupled plasma atomic emission spectrometer (ICP-AES) for calculating the $Ca^{2+}$ binding ability. The results are shown in Table 3 and FIG. 2.

TABLE 3

$Ca^{2+}$ Binding Ability of Extra- and Intra-Cellular Proteins

| | | $Ca^{2+}$ binding ability (mg $Ca^{2+}$/mg protein) | |
|---|---|---|---|
| Strain codes | Strains | Intracellular protein | Extracellular protein |
| IC-5 | 98.764% of 16 S DNA similarity with *Anoxybacillus kamchatkensis* JW/VK-KG4$^T$ | 0.012 | 0.034 |
| LJ-B | 98.949% of 16 S DNA similarity with *Anoxybacillus mongoliensis* T4$^T$ | 0.005 | 0.069 |
| AT-A1 | 100.00% of 16 S DNA similarity with *Meiothermus ruber* DSM 1279$^T$ | 0.006 | 0.032 |
| AT-A2 | *Tepidimonas fonticaldi* sp. nov. | 0.011 | 0.327 |
| BCRC 17110 | *Thermus aquaticus* BCRC 17110 | 0.005 | 0.082 |

Figure 2:
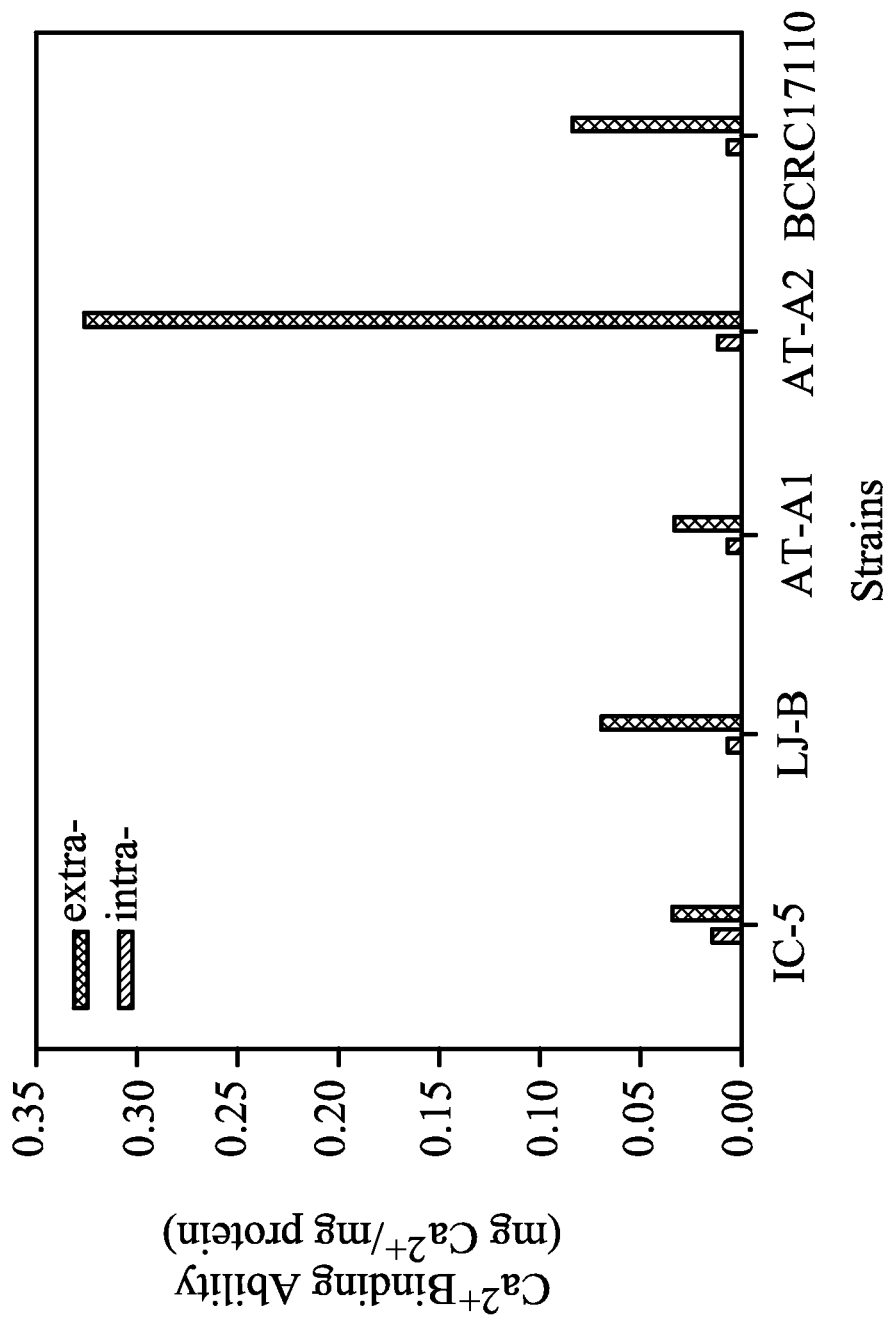
FIG. 2 is a bar graph showing the $Ca^{2+}$ binding ability of intra- and extra-cellular proteins of several thermophilic strains.

As shown in Table 3 and FIG. 2, the $Ca^{2+}$ binding ability of the extracellular proteins was much more significant than that of the intracellular proteins. Meanwhile, the extracellular proteins of Strain AT-A2 showed 0.327 mg of $Ca^{2+}$/mg protein, the best binding ability among the strains. Regarding the other strains, the extracellular proteins merely showed $Ca^{2+}$ binding ability of less than 0.1 mg of $Ca^{2+}$/mg protein.

$Ca^{2+}$ Binding Ability Under Various Conditions

An experiment was designed for investigating the effects of environmental factors, like temperature, pressure, pH value etc., on the $Ca^{2+}$ binding ability of the extracellular proteins from some of the thermophilic bacteria listed in Table 3.

The experiment included the three following groups:

Group 1: The extracellular proteins 50 ppm were treated respectively under a pressure of 10 atm, 30 atm and 50 atm, at 25° C., pH 7 for 10 minutes;

Group 2: The extracellular proteins 50 ppm were treated respectively under a pH 2, pH 4, pH 6, pH 7, pH 8 and pH 10 at 25° C., 1 atm for 10 minutes; and Group 3: The extracellular proteins 50 ppm were treated respectively under a temperature of 100° C., 125° C., and 150° C., at 1 atm, pH 7 for 10 minutes.

The treated proteins 50 ppm were separately mixed with a 100 ppm calcium ion solution prepared by $CaCl_2 \cdot 2H_2O$ in a ratio of 1:1. The mixture was heated in a 100° C. water bath for 10 minutes. The mixture was then filtered through an ultrafiltration system with a 3 KDa membrane to capture the proteins. The filtrate was then diluted with deionized water to reach the detection limit (0~5 ppm). The $Ca^{2+}$ concentration left in the filtrate was analyzed by an inductively coupled plasma atomic emission spectrometer (ICP-AES) for calculating the $Ca^{2+}$ binding ability. The results are shown in FIGS. 3-5.

Figure 3:
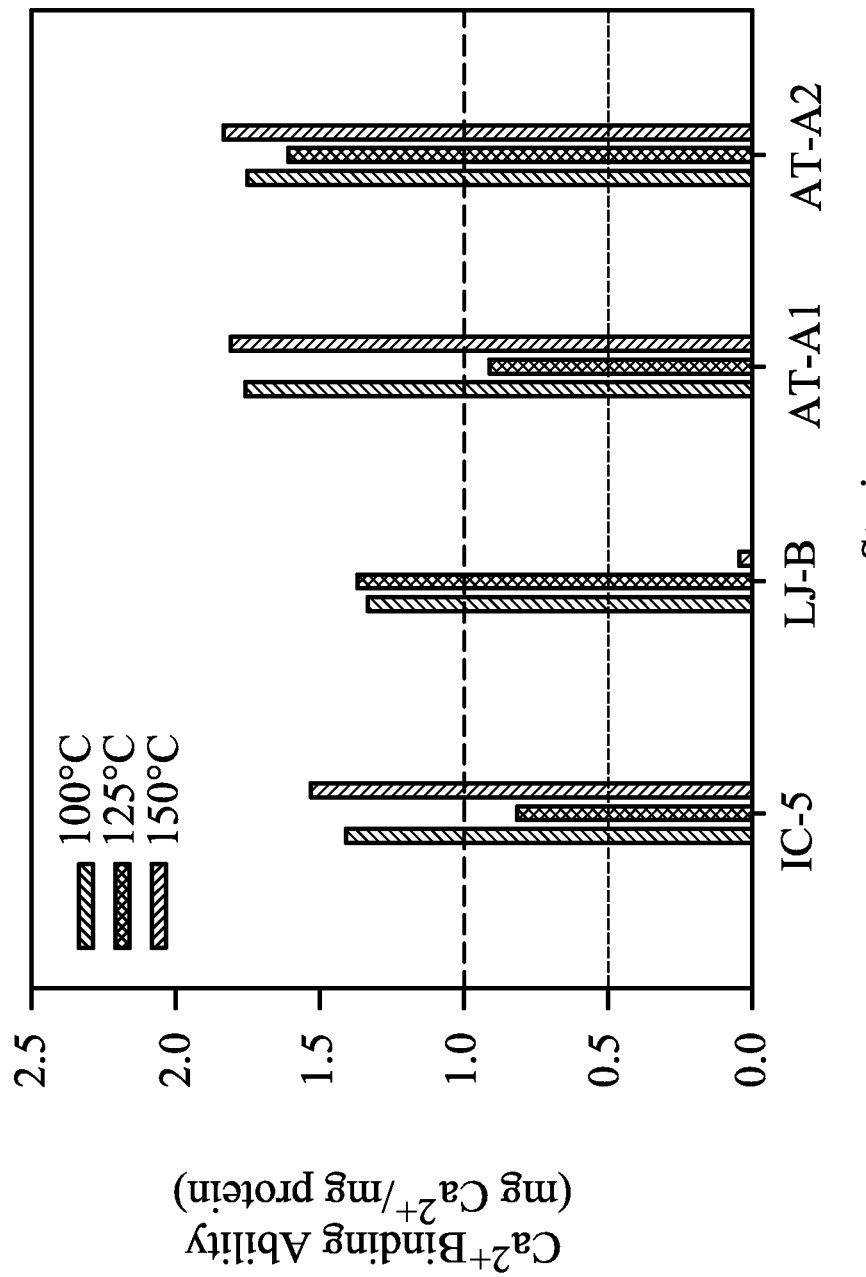
FIG. 3 is a bar graph showing the $Ca^{2+}$ binding ability of extracellular proteins of several thermophilic strains under various temperature conditions.
Figure 4:
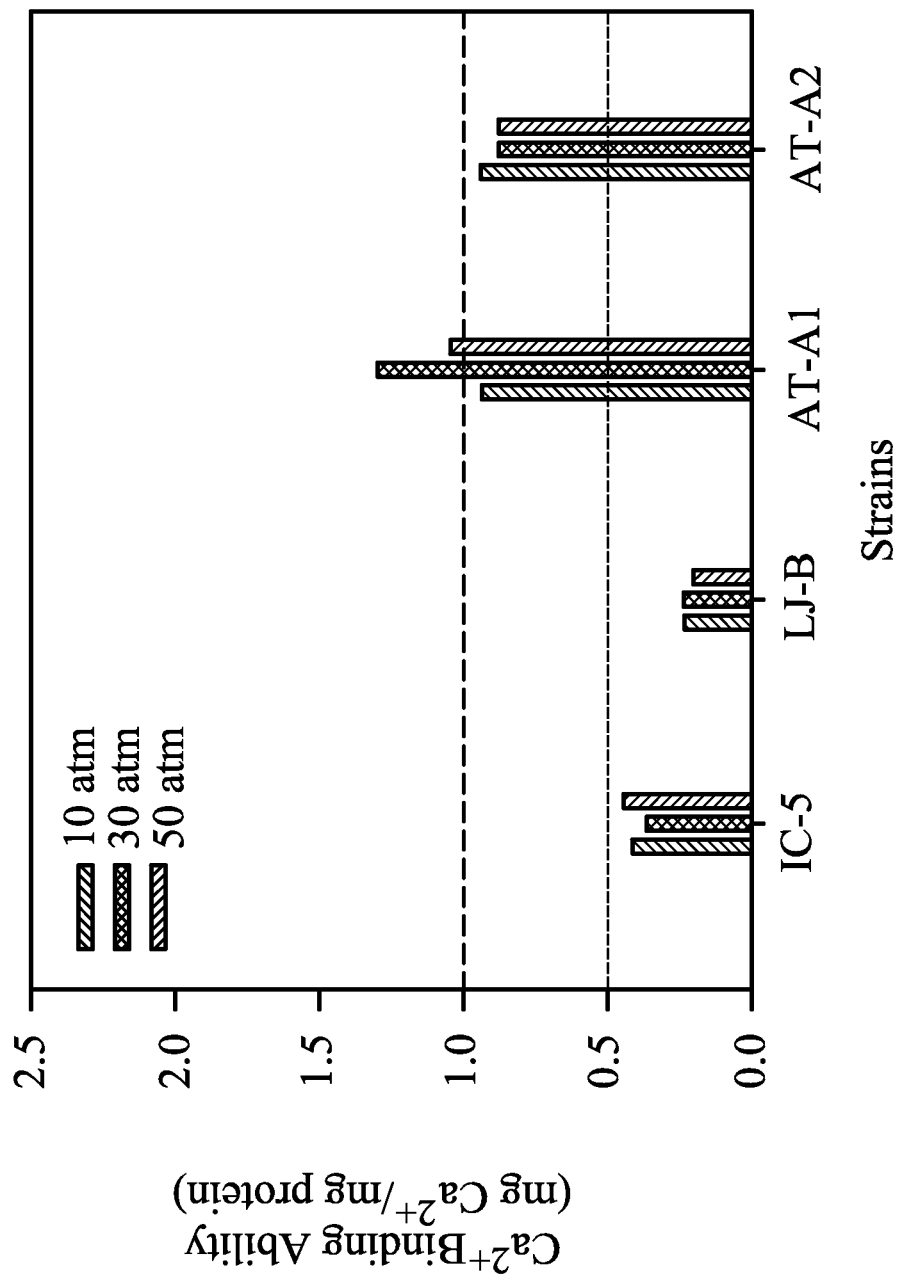
FIG. 4 is a bar graph showing the $Ca^{2+}$ binding ability of extracellular proteins of several thermophilic strains under various pressure conditions.
Figure 5:
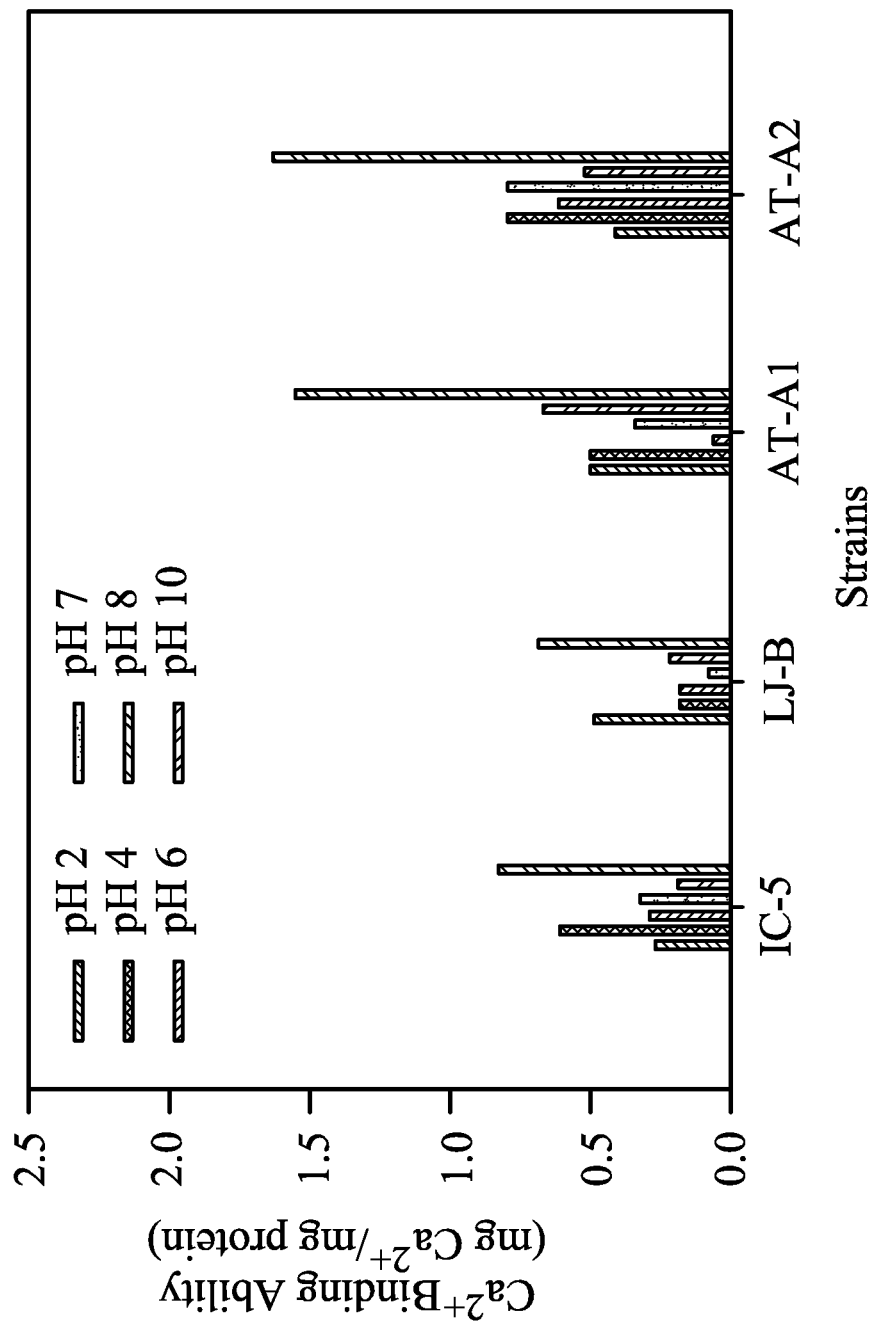
FIG. 5 is a bar graph showing the $Ca^{2+}$ binding ability of extracellular proteins of several thermophilic strains under various pH value conditions.
Figure 8:
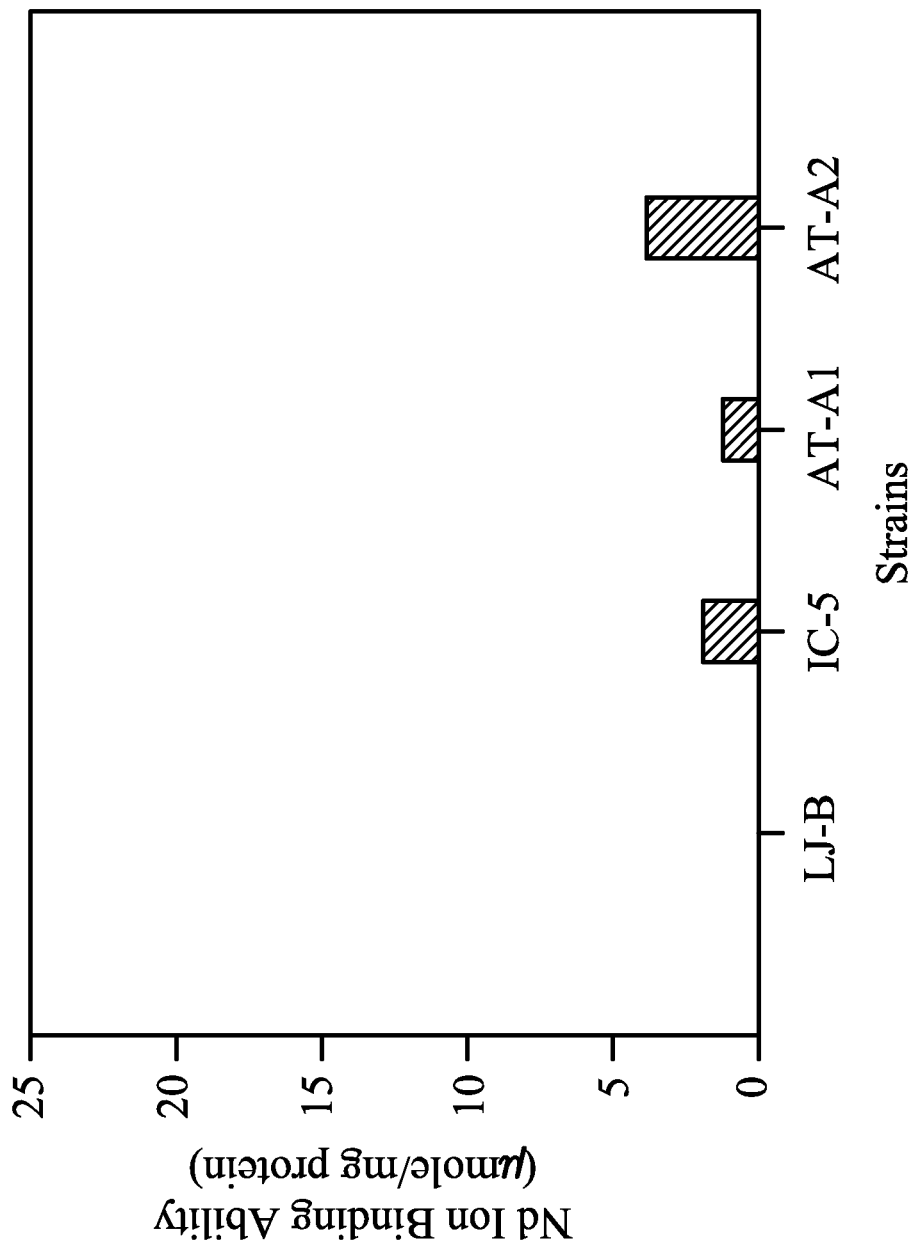
FIG. 8 is a bar graph showing the neodymium (Nd) ion binding ability of extracellular proteins of several thermophilic strains.
Figure 9:
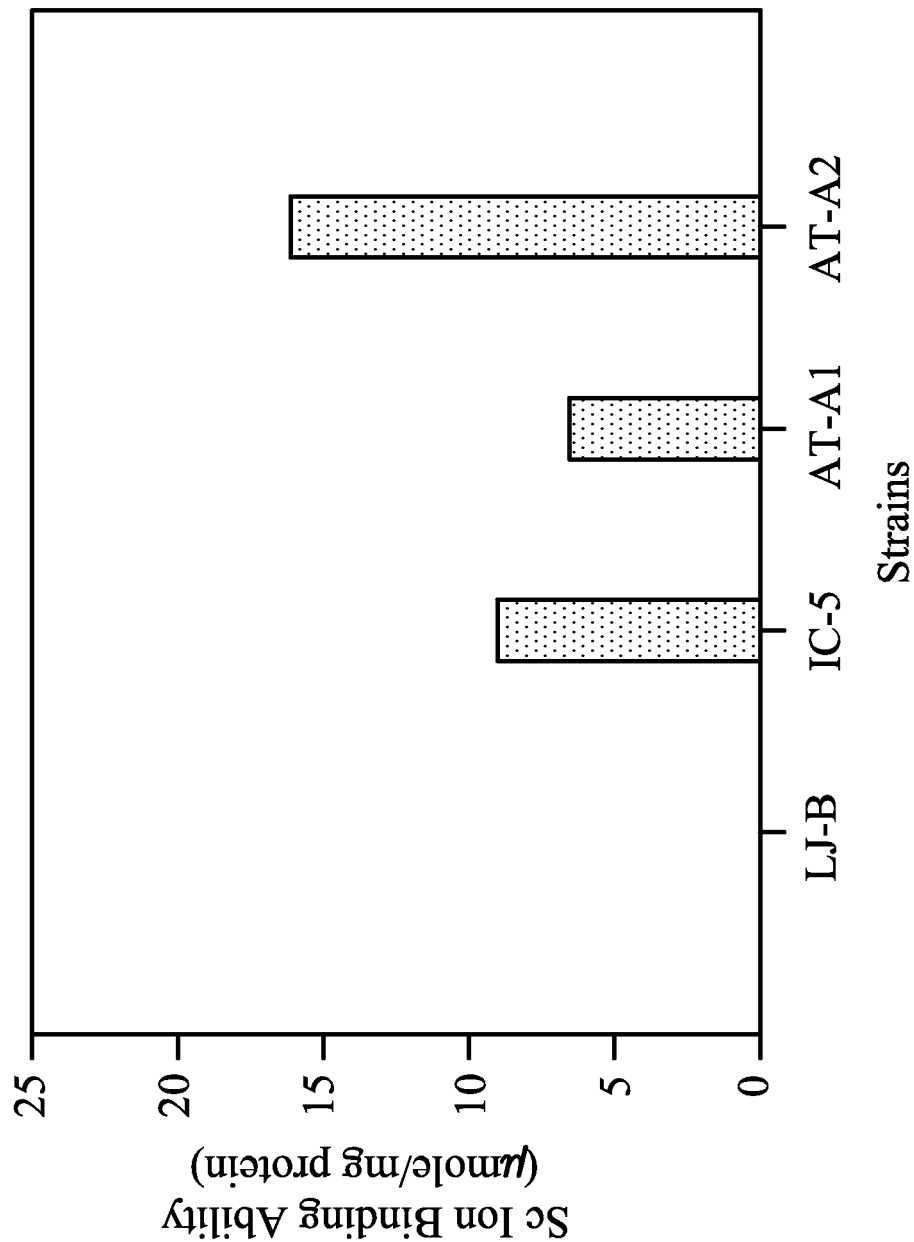
FIG. 9 is a bar graph showing the scandium (Sc) ion binding ability of extracellular proteins of several thermophilic strains.

In FIGS. 3~5, the extracellular proteins from Strain AT-A2 (*Tepidimonas fonticaldi* sp. nov.) showed excellent $Ca^{2+}$ binding ability under high temperatures, high pressure or broad pH values.

Bi- and Tri-Valent Metal Ion Binding Ability

An experiment was designed for investigating the bi- and tri-valent metal ion binding ability of the extracellular proteins from some of the thermophilic bacteria listed in Table 3.

The experiment included the two following groups:

Group A: The extracellular proteins 10 ppm were mixed with a first standard solution 10 ppm in a ratio of 1:1 and reacted at 100° C., pH 2 for 20 minutes. The first standard solution included metal ions of cerium (Ce), dysprosium (Dy), erbium (Er), europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb) and yttrium (Y). The binding ability is shown in a unit of μ mole metal ions/mg proteins in FIGS. 6~11.

Figure 12:
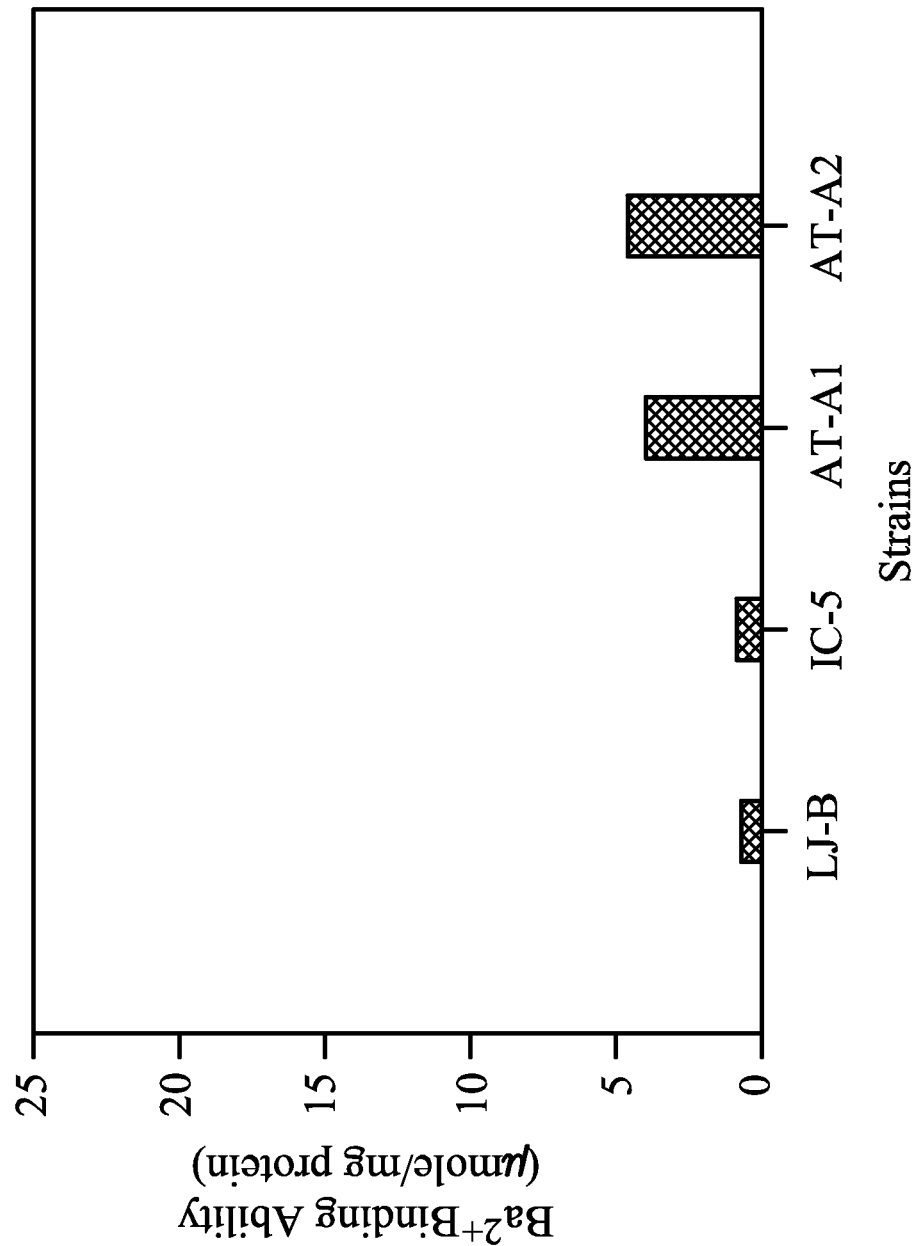
FIG. 12 is a bar graph showing the barium (Ba) ion binding ability of extracellular proteins of several thermophilic strains.
Figure 13:
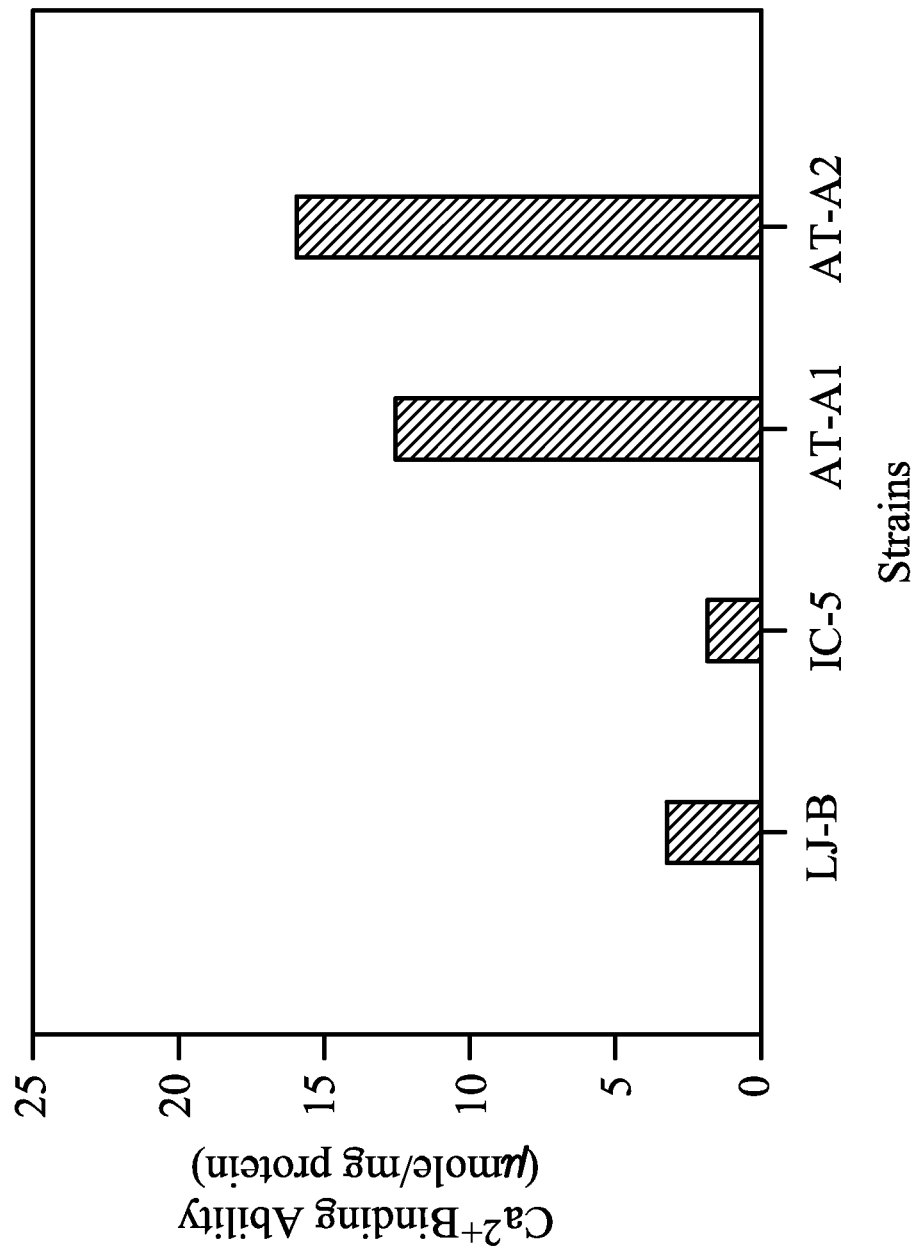
FIG. 13 is a bar graph showing the $Ca^{2+}$ binding ability of extracellular proteins of several thermophilic strains.

Group B: The extracellular proteins 10 ppm were mixed with a second standard solution 10 ppm in a ratio of 1:1 and reacted at 100° C., pH 2 for 20 minutes. The second standard solution included metal ions of silver (Ag), aluminium (Al), boron (B), barium (Ba), bismuth (Bi), calcium (Ca), cadmium (Cd), cobalt (Co), chromium (Cr), copper (Cu), iron (Fe), gallium (Ga), indium (In), potassium (K), lithium (Li), magnesium (Mg), manganese (Mn), sodium (Na), nickel (Ni), lead (Pb), strontium (Sr), thallium (Tl) and zinc (Zn). The $Ba^{2+}$ and $Ca^{2+}$ binding ability is shown in a unit of μ mole metal ions/mg protein in FIGS. 12~13.

As given in FIGS. 6~13, the extracellular proteins from Strain AT-A2 (*Tepidimonas fonticaldi* sp. nov.) showed excellent binding ability broadly to bi- and tri-valent metal ions.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for inhibiting salt formation, comprising: culturing an isolated thermophilic bacterium in a culture medium; separating cultured thermophilic bacterium from the culture medium to obtain a supernatant comprising a mixture of extracellular proteins excreted by the cultured thermophilic bacterium; concentrating the supernatant comprising the mixture of extracellular proteins to 50 ppm; and contacting the concentrated supernatant comprising the mixture of extracellular proteins with a metal ion-containing solution to form a complex of the extracellular protein(s) and the metal ion(s), at a ratio of 1:1 of the supernatant to the metal ion-containing solution, wherein the isolated thermophilic bacterium is *Tepidimonas fonticaldi* sp. nov. internationally deposited in the Korean Collection of Type Culture (KCTC) with deposit number of KCTC 12528BP.

2. The method of claim 1, wherein the metal ion is a bi- or tri-valent metal ions.

3. The method of claim 1, wherein the metal ion comprises cerium (Ce), dysprosium (Dy), erbium (Er), europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb), yttrium (Y), silver (Ag), aluminium (Al), boron (B), barium (Ba), bismuth (Bi), calcium (Ca), cadmium (Cd), cobalt (Co), chromium (Cr), copper (Cu), iron (Fe), gallium (Ga), indium (In), potassium (K), lithium (Li), magnesium (Mg), manganese (Mn), sodium (Na), nickel (Ni), lead (Pb), strontium (Sr), thallium (Tl), or zinc (Zn).

4. The method of claim 1, wherein the method is performed at a temperature between 75~150° C.

5. The method of claim 1, wherein the method is performed at a pressure between 1~50 atm.

6. The method of claim 1, wherein the method is performed at a pH 2~10.

7. The method of claim 1, wherein the metal ion-containing solution comprises geothermal waters, boiler solutions, industrial waste, or hard water.

8. The method of claim 1, wherein the method is applied to the treatment of boiler equipment, water pipelines, geothermal wells, industrial wastewater, or hard water.

9. A method for treating high temperature wastewater, comprising: culturing an isolated thermophilic bacterium in a culture medium; separating cultured thermophilic bacterium from the culture medium to obtain a supernatant comprising a mixture of extracellular proteins excreted by the cultured thermophilic bacterium; concentrating the supernatant comprising the mixture of extracellular proteins to 50 ppm; contacting the concentrated supernatant comprising the mixture of extracellular proteins with a metal ion-containing solution to form a complex of the extracellular protein(s) and the metal ion(s), at a ratio of 1:1 of the supernatant to the metal ion-containing solution, wherein the isolated thermophilic bacterium is *Tepidimonas fonticaldi* sp. nov. internationally deposited in the Korean Collection of Type Culture (KCTC) with deposit number of KCTC 12528BP.

10. The method of claim 9, wherein the metal ion is a bi- or tri-valent metal ions.

11. The method of claim 9, wherein the metal ion comprises cerium (Ce), dysprosium (Dy), erbium (Er), europium (Eu), gadolinium (Gd), holmium (Ho), lanthanum (La), lutetium (Lu), neodymium (Nd), praseodymium (Pr), scandium (Sc), samarium (Sm), terbium (Tb), thorium (Th), thulium (Tm), uranium (U), ytterbium (Yb), yttrium (Y), silver (Ag), aluminium (Al), boron (B), barium (Ba), bismuth (Bi), calcium (Ca), cadmium (Cd), cobalt (Co), chromium (Cr), copper (Cu), iron (Fe), gallium (Ga), indium (In), potassium (K), lithium (Li), magnesium (Mg), manganese (Mn), sodium (Na), nickel (Ni), lead (Pb), strontium (Sr), thallium (Tl), or zinc (Zn).

12. The method of claim 9, wherein the method is performed at a temperature between 75~150° C.

13. The method of claim 9, wherein the method is performed at a pressure between 1~50 atm.

14. The method of claim 9, wherein the method is performed at a pH 2~10.

15. The method of claim 9, wherein the metal ion-containing solution comprises geothermal waters, boiler solutions, industrial waste, or hard water.

16. The method of claim 9, wherein the method is applied to the treatment of boiler equipment, water pipelines, geothermal wells, industrial wastewater, or hard water.

17. The method according to claim 1, wherein culturing includes growing the isolated thermophilic bacterium at 55° C. for 3 to 5 days.

18. The method according to claim 1, wherein the culture medium comprises digested casein, digested soybean meal, dextrose and sodium chloride.

19. The method according to claim 9, wherein culturing includes growing the isolated thermophilic bacterium at 55° C. for 3 to 5 days.

20. The method according to claim 19, wherein the culture medium comprises digested casein, digested soybean meal, dextrose and sodium chloride.

* * * * *

SEQUENCE LISTING

<160> NUMBER OF SEQ ID NOS: 3

<210> SEQ ID NO 1
<211> LENGTH: 1276
<212> TYPE: DNA
<213> ORGANISM: Tepidimonas thermarum AA-1

<400> SEQUENCE: 1

```
gggtgctgac gagtggcgaa cgggtgagta atgcatcgga acgtgcccag aggtgggga      60 taacgcagcg aaagctgtgc taataccgca tgtgatctga ggatgaaagc gggggaccaa     120
gcagcaatgt ttggcctcgc gcctctggag cggccgatgt cagattaggt agttggtggg    180
gtaaaggcct accaagccga cgatctgtag ctggtctgag aggacgacca gccacactgg    240
gactgagaca cggcccagac tcctacggga ggcagcagtg gggaattttg acaatgggc     300 gcaagcctga tccagcaatg ccgcgtgcgg gaagaaggcc ttcgggttgt aaaccgcttt    360
tgtacggaac gaaaaggctc tggctaatac ctggggctga tgacggtacc gtaagaataa    420
gcaccggcta actacgtgcc agcagccgcg gtaatacgta gggtgcgagc gttaatcgga    480
attactgggc gtaaagcgtg cgcaggcggt cttgtaagac agaggtgaaa tccctgggct    540
caacctagga atggcctttg tgactgcaag gctggagtgc ggcagagggg gatagaattc    600
cgcgtgtagc agtgaaatgc gtagatatgc ggaggaacac cgatgcgaa ggcagtcccc    660 tgggcctgca ctgacgctca tgcacgaaag cgtggggagc aaacaggatt agatacctg     720 gtagtccacg ccctaaacga tgtcgactgg ttgttgggcc ttaggtggct cagtaacgaa    780
gctaacgcgt gaagtcgacc gcctgggag tacggccgca aggttgaaac tcaaaggaat    840 tgacgggggac ccgcacaagc ggtggatgat gtggtttaat tcgatgcaac gcgaaaaacc   900
ttacctaccc ttgacatgcc aggaatcctg cagagatgtg ggagtgctcg caagagagcc    960
tggacacagg tgctgcatgg ctgtcgtcag ctcgtgtcgt gagatgttgg gttaagtccc   1020
gcaacgagcg caacccttgc cattagttgc tacgaaaggg cactctaatg ggactgccgg   1080
tgacaaaccg gaggaaggtg gggatgacgt caagtcctca tggcccttat gggtagggct   1140
```

```
acacacgtca tacaatggcc ggtacagagg gctgccaacc cgcgaggggg agccaatccc    1200
gtaaaaccgg tcgtagtccg gattgcagtc tgcaactcga ctgcatgaag tcggaatcgc    1260
tagtaatcgc ggatca                                                   1276

<210> SEQ ID NO 2
<211> LENGTH: 20
<212> TYPE: DNA
<213> ORGANISM: Artificial Sequence
<220> FEATURE:
<223> OTHER INFORMATION: Synthetic primer FD1

<400> SEQUENCE: 2
agagtttgat cctggctcag                                                20

<210> SEQ ID NO 3
<211> LENGTH: 17
<212> TYPE: DNA
<213> ORGANISM: Artificial Sequence
<220> FEATURE:
<223> OTHER INFORMATION: Synthetic primer RD1

<400> SEQUENCE: 3
aaggaggtga tccagcc                                                   17
```